(12) United States Patent
Chen et al.

(10) Patent No.: US 9,416,229 B2
(45) Date of Patent: Aug. 16, 2016

(54) DIANHYDRIDE AND POLYIMIDE

(71) Applicant: INDUSTRIAL TECHNOLOGY RESEARCH INSTITUTE, Hsinchu (TW)

(72) Inventors: Wei-Hong Chen, Zhubei (TW); Po-Jen Yang, Taichung (TW); Chih-Hsiang Lin, Taipei (TW); Meng-Hsin Chen, Xinpi Township (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 14/722,880

(22) Filed: May 27, 2015

(65) Prior Publication Data

US 2015/0344626 A1    Dec. 3, 2015

Related U.S. Application Data

(60) Provisional application No. 62/003,658, filed on May 28, 2014.

(51) Int. Cl.
| | | |
|---|---|---|
| *C08G 73/16* | (2006.01) | |
| *C08G 73/10* | (2006.01) | |
| *C07D 307/89* | (2006.01) | |
| *C07D 407/14* | (2006.01) | |

(52) U.S. Cl.
CPC .......... *C08G 73/1071* (2013.01); *C07D 307/89* (2013.01); *C07D 407/14* (2013.01); *C08G 73/1085* (2013.01); *C08G 73/16* (2013.01)

(58) Field of Classification Search
CPC ............. Y10T 428/1023; C08G 73/10; C08G 73/1082; C08G 73/1071; C08G 73/1085; C08G 73/16
See application file for complete search history.

(56) References Cited

U.S. PATENT DOCUMENTS

| | | |
|---|---|---|
| 6,303,742 B1 | 10/2001 | Okada et al. |
| 6,689,899 B2 | 2/2004 | Okada et al. |
| 6,800,381 B2 | 10/2004 | Cho et al. |
| 6,835,468 B2 | 12/2004 | Cho et al. |
| 7,019,104 B1 | 3/2006 | Okada et al. |
| 7,455,948 B2 | 11/2008 | Taniguchi et al. |
| 7,476,476 B2 | 1/2009 | Suwa |
| 7,507,518 B2 | 3/2009 | Fujita et al. |
| 7,524,919 B2 | 4/2009 | Hoover |
| 7,629,400 B2 | 12/2009 | Hyman |
| 7,642,315 B2 | 1/2010 | Davis et al. |
| 7,649,073 B2 | 1/2010 | Davis et al. |
| 7,700,696 B2 | 4/2010 | Van De Grampel et al. |
| 7,709,581 B2 | 5/2010 | Glasgow et al. |
| 7,718,755 B2 | 5/2010 | Chatterjee et al. |
| 7,807,772 B2 | 10/2010 | Chatterjee et al. |
| 7,977,400 B2 | 7/2011 | Taniguchi et al. |
| 8,294,040 B2 | 10/2012 | Shimizu et al. |
| 8,470,446 B2 | 6/2013 | Wu et al. |

(Continued)

FOREIGN PATENT DOCUMENTS

| | | |
|---|---|---|
| CN | 101113205 A | 1/2008 |
| CN | 102352039 A | 2/2012 |

(Continued)

OTHER PUBLICATIONS

Hasegawa et al (Fluorene-Containing Poly(ester imide)s and their Application to Positive-Type Photosensitive Heat-Resistant Materials, Macromolecular Materials and Engineering, vol. 296, Issue 11, pp. 1002-1017), Jul. 1, 2011.*

(Continued)

*Primary Examiner* — Gregory Listvoyb
(74) *Attorney, Agent, or Firm* — Birch, Stewart, Kolasch & Birch, LLP

(57) ABSTRACT

A dianhydride and a polyimide formed by the same are provided. The dianhydride has a chemical structure represented below:

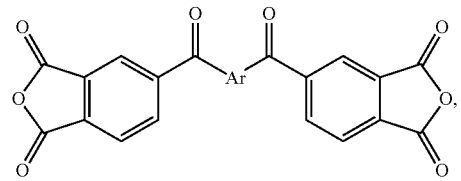

wherein Ar is a fluorene-containing group. The dianhydride can be polymerized with a diamine to form a polyimide with a repeating unit of a chemical formula:

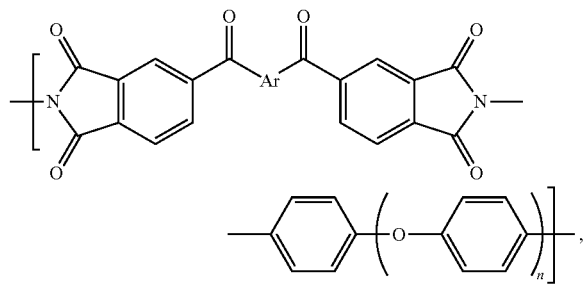

wherein Ar is the fluorene-containing group, and n is a positive integer from 1 to 5. The polyimide simultaneously has excellent thermal stability and hot workability, and can therefore be applied in several industries.

4 Claims, No Drawings

(56) References Cited

U.S. PATENT DOCUMENTS

| | | |
|---|---|---|
| 8,497,025 B2 | 7/2013 | Uera et al. |
| 8,536,282 B2 | 9/2013 | Lens et al. |
| 2002/0019558 A1 | 2/2002 | Okada et al. |
| 2002/0051895 A1 | 5/2002 | Cho et al. |
| 2003/0035917 A1 | 2/2003 | Hyman |
| 2003/0099838 A1 | 5/2003 | Cho et al. |
| 2005/0014876 A1 | 1/2005 | Fujita et al. |
| 2006/0110680 A1 | 5/2006 | Taniguchi et al. |
| 2006/0159839 A1 | 7/2006 | Suwa |
| 2007/0065615 A1 | 3/2007 | Odle et al. |
| 2007/0066739 A1 | 3/2007 | Odle et al. |
| 2007/0066740 A1 | 3/2007 | Odle et al. |
| 2007/0066741 A1 | 3/2007 | Donovan et al. |
| 2007/0142569 A1 | 6/2007 | Donovan et al. |
| 2007/0149629 A1 | 6/2007 | Donovan et al. |
| 2008/0004404 A1 | 1/2008 | Van De Grampel et al. |
| 2008/0081884 A1 | 4/2008 | Glasgow et al. |
| 2008/0081893 A1 | 4/2008 | Hoover et al. |
| 2008/0081895 A1 | 4/2008 | Lens et al. |
| 2008/0108723 A1 | 5/2008 | Taniguchi et al. |
| 2008/0118729 A1 | 5/2008 | Goyette et al. |
| 2008/0119619 A1 | 5/2008 | Mullen |
| 2008/0119631 A1 | 5/2008 | Mullen |
| 2008/0153994 A1 | 6/2008 | Lens et al. |
| 2008/0306294 A1 | 12/2008 | Lens et al. |
| 2008/0312373 A1 | 12/2008 | Davis et al. |
| 2008/0312374 A1 | 12/2008 | Davis et al. |
| 2009/0008142 A1 | 1/2009 | Shimizu et al. |
| 2009/0105444 A1 | 4/2009 | Chatterjee et al. |
| 2009/0123747 A1 | 5/2009 | Fujimaru et al. |
| 2009/0186966 A1 | 7/2009 | Gallucci et al. |
| 2009/0286094 A1 | 11/2009 | Uera et al. |
| 2009/0326181 A1 | 12/2009 | Lens et al. |
| 2010/0120993 A1 | 5/2010 | Chatterjee et al. |
| 2010/0145002 A1 | 6/2010 | Hasegawa et al. |
| 2011/0257360 A1 | 10/2011 | Hasegawa et al. |
| 2012/0251949 A1 | 10/2012 | Miyabe et al. |
| 2012/0308835 A1 | 12/2012 | Hong et al. |

FOREIGN PATENT DOCUMENTS

| | | |
|---|---|---|
| CN | 102617382 A | 8/2012 |
| CN | 102702562 A | 10/2012 |
| CN | 103102489 A | 5/2013 |
| EP | 2 535 341 A1 | 12/2012 |
| JP | 2007-91701 A | 4/2007 |
| JP | 2009-57232 A | 3/2009 |
| TW | 214561 B | 10/1993 |
| WO | WO 90/03405 A1 | 4/1990 |
| WO | WO 95/02627 A1 | 1/1995 |
| WO | WO 2012/088759 A1 | 7/2012 |

OTHER PUBLICATIONS

USPTO structure search, Jan. 2016.*

An et al., "Synthesis and Properties of Fluorene-Based Polyimide Adhesives", Polymer Engineering and Science, vol. 51, Issue 8, Aug. 1, 2011, pp. 1533-1540.

Brinkmann et al., Structure and Morphology in Highly Oriented Films of Poly(9,9-bis(n-octyl)fluorene-2, 7-diyl) and Poly(9,9-bis(2-ethylhexyl)fluorene-2, 7-diyl) Grown on Friction . . . Macromolecules, vol. 42, No. 21, 2009 (Published on Web Aug. 25, 2009), pp. 8298-8306.

Fang et al., "Novel Sulfonated Polyimides as Polyelectrolytes for Fuel Cell Application. 1. Synthesis, Proton Conductivity, and Water Stability of Polyimides from 4,4'-Diaminodiphenyl Ether-2,2'-disulfonic Acid", Macromolecules, vol. 35, No. 24, 2002 (published on Web Oct. 26, 2002), pp. 9022-9028.

Oishi et al., "Synthesis of Fluorine-Containing Wholly Alicyclic Polyimides", Journal of Photopolymer Science and Technology, vol. 16, No. 2, 2003, pp. 263-266.

Xu et al., "A novel fluorene-based cardo polyimide containing acridine for electroluminescent devices", Synthetic Metals, vol. 132, 2003, pp. 145-149.

Xu et al., "Novel polyimide containing fluorene and perylene units in the backbone", Journal of Materials Science Letters, vol. 21, 2002, pp. 1903-1905.

Hasegawa et al., "γ-Butyrolactone-processable high-modulus poly-(ester imide)s," Polymer International, vol. 61, 2012 (published online Nov. 10, 2011), 2 pages.

Taiwanese Office Action and Search Report, dated Mar. 9, 2016, for Taiwanese Application No. 104117124.

* cited by examiner

DIANHYDRIDE AND POLYIMIDE

CROSS REFERENCE TO RELATED APPLICATIONS

This Application claims the benefit of U.S. Provisional Application No. 62/003,658, filed on May 28, 2014, the entireties of which are incorporated by reference herein.

TECHNICAL FIELD

The disclosure relates to a polyimide, and a dianhydride used to form the polyimide.

BACKGROUND

In general, Polyimide has been widely used in various technical fields because it exhibits excellent high-temperature resistance, excellent chemical-resistance properties, high insulation, and high mechanical strength. Unfortunately, PI is difficult to dissolve in common solvents, because of its non-polar groups, such as aromatic rings and imino groups. However, close packing of molecular backbones causes difficulty in industrial manufacturing processes of PI and some problems in application. Therefore, thermoplastic polyimide (TPI) has been developed. Determining the performance of PI due to the monomer structure, some soft groups were usually introduced into TPI. However, for subsequent processing at high temperatures, it may lead to change in its structure and thermal properties, which reduce the heat resistance of the polymer and affect the performance thereof.

Accordingly, a novel PI monomer to meet the requirements of thermoplastic ability and heat-resistance is called-for.

SUMMARY

In accordance with one embodiment of the disclosure, a dianhydride is provided. The dianhydride has a chemical structure represented by formula 1:

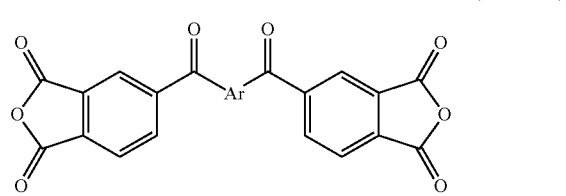

(Formula 1)

In formula 1, Ar is a fluorene-containing group.

In accordance with another embodiment of the disclosure, a polyimide is provided. The polyimide has a repeating unit as represented by formula 2:

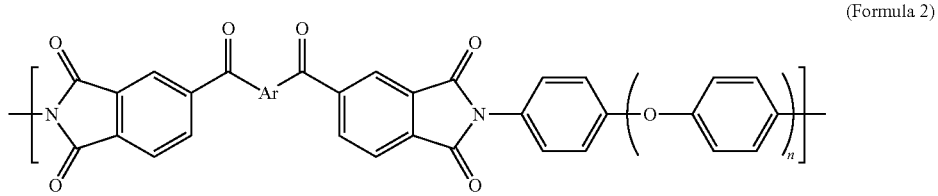

(Formula 2)

In formula 2, Ar is a fluorene-containing group, and n is a positive integer from 1 to 5.

A detailed description is given in the following embodiments with reference to the accompanying drawings.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are shown schematically in order to simplify the drawing.

According to the embodiments of the disclosure, the disclosure provides a dianhydride, which has a chemical structure represented by formula 1:

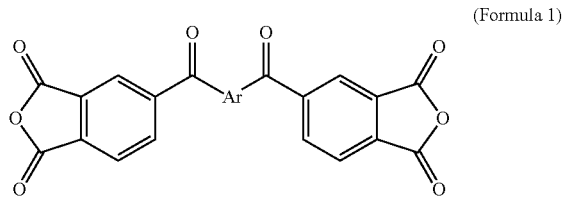

(Formula 1)

In formula 1, Ar may be a fluorene-containing group.

In some embodiments, the fluorenyl group may be one of the groups shown in formula 3 to formula 5:

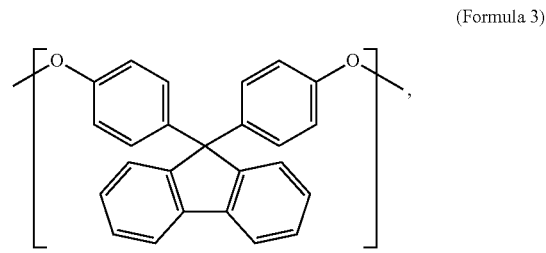

(Formula 3)

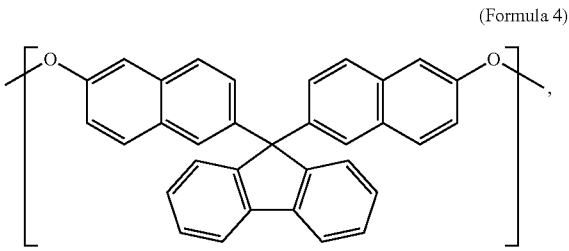

(Formula 4)

(Formula 5)

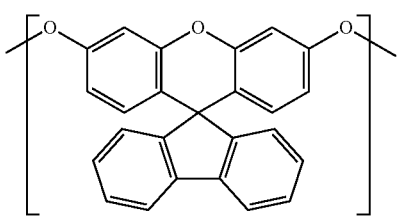

In accordance with another embodiment of the disclosure, the dianhydride can be polymerized with a diamine to form a polyimide with a repeating unit of a chemical formula 2:

(Formula 2)

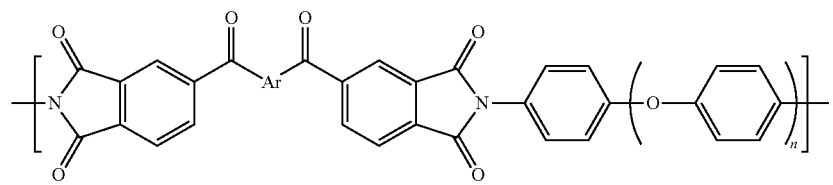

In formula 2, Ar may be a fluorene-containing group, and n is a positive integer from 1 to 5.

In a embodiment, the fluorenyl group may be one of the groups shown in formula 3 to formula 5:

(Formula 3)

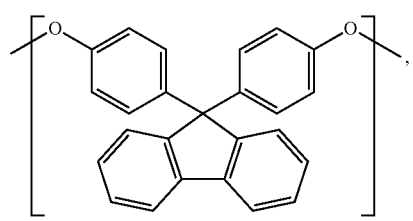

(Formula 4)

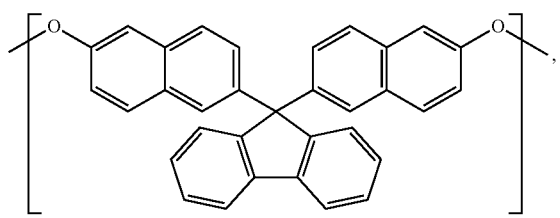

(Formula 5)

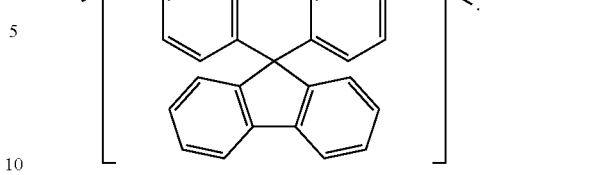

The dianhydrides mentioned above can be polymerized with a diamine to form a polyimide, but is not limited thereto. For example, the dianhydride can also be polymerized with a glycol to form a polyester. If the dianhydride is polymerized to form a polyimide with a diamine, it may have a soft functional group with a chemical structure represented by formula 6:

(Formula 6)

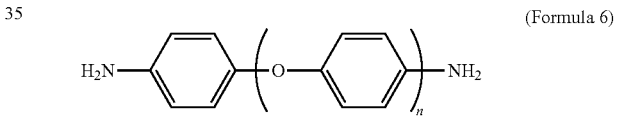

The reaction of the aforementioned dianhydrides with diamines is shown in Formula 7. In Formula 7, n is the number of repetitions. In one embodiment of the disclosure, the starting solids content of the reaction of the dianhydride and the diamine in a solvent is between 15 wt % and 30 wt %. If the solid content is too low, problems can arise, such as the molecular collision frequency being lower and the reaction not conducting easily, leading to low polymerization. If the solid content is too high, it causes a high solution viscosity and has difficulty stirring uniformly. Forming PI reaction contains two sections: in the front ring-opening, the reaction temperature is between 0 and 25° C. (room temperature), and in the ring-closing, reaction temperature is between 180 and 210° C. The product PI Formula 7 has a weight average molecular weight of 20,000 to 80,000. If the weight average molecular weight of PI is too high to result in decreased solubility for the solvent, it is not conducive to the later application of a film formation process. If the weight average molecular weight of PI is too low, it causes film-forming to be difficult.

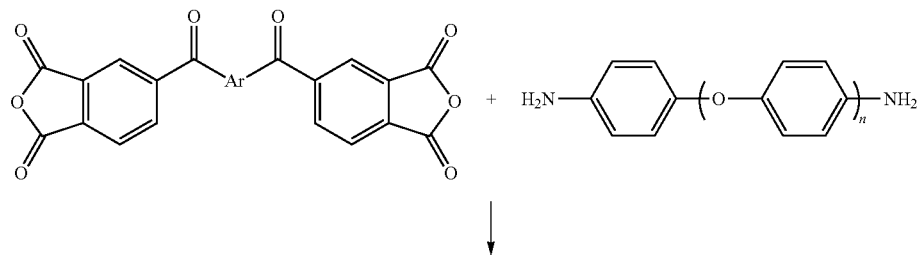

(Formula 7)

In one embodiment of the disclosure, first of all, PI can be melted to produce a thick film, and then the film can be stretched in the MD and TD directions to form a thin film. By adjusting the stretching temperature/ratio/speed and thermal setting temperature/time, some better film properties can be obtained. i.e. the heat resistance of the film can be greater than 310° C. and the ratio of thermal expansion coefficient in the length direction (MD direction) to thermal expansion coefficient in the width direction (TD direction) can be less than or equal to 20/10. Therefore, the aforementioned PI has the advantages of heat resistance (high thermal decomposition temperature and a high glass transition temperature) and excellent hot workability.

Below, exemplary embodiments will be described in detail with reference to the accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

In the following examples, the measurement method of a weight average molecular weight (Mw) of PI was obtained by gel permeation chromatography (GPC). A molecular weight distribution of PI is measured using a refractive index detector (RI Detector, Instruments Model Jasco PU2089) and dichloromethane as a solvent and polystyrene as a standard sample (Viscotek PolyCAL standard sample, purchased from Ana-Lab corp.).

Example 1

Synthesis of Phenyl-Fluorene Monomer 1,2,4-trimellitic anhydride acid chloride (120 mmole) was dissolved in 60 mL of anhydrous THF. Fluorene-9-bisphenol (60 mmole) and pyridine (14.5 mL) were dissolved in another 100 mL of anhydrous THF, and then slowly and dropwise added into the 1,2,4-trimellitic anhydride acid chloride solution under nitrogen, and then completely reacted at 40° C. for 12 hours. The reaction result was filtered to remove the salt thereof, and the solvent of the filtrate was removed by a rotary evaporator to obtain a solid. The solid was washed with n-hexane and re-crystallized from acetic anhydride two times to obtain a white solid (yield=75%). The 1H NMR spectrum of the white solid is listed below: 1H NMR (CDCl3, 400 MHz, ppm): 8.77 (s, 2H), 8.69 (d, 2H), 8.14 (d, 2H), 7.82 (d, 2H), 7.43 (m, 4H). The above-mentioned reaction is represented as:

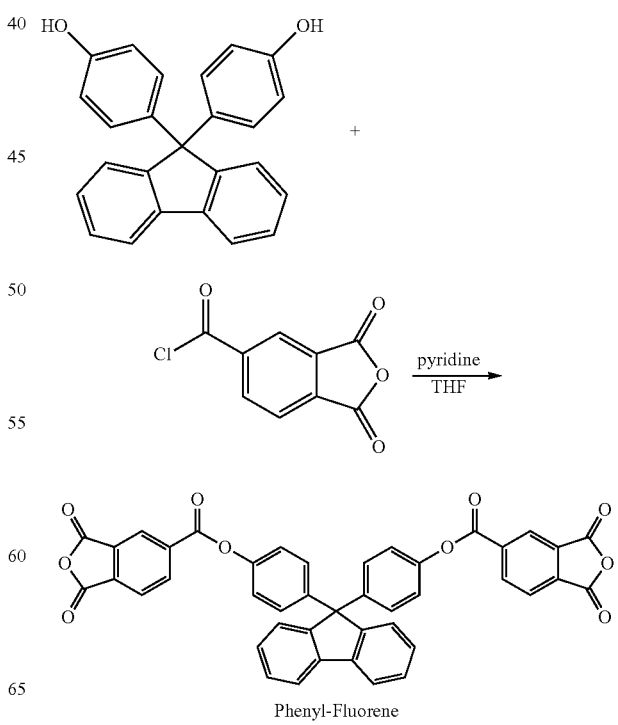

Phenyl-Fluorene

Example 2

Synthesis of Naphthyl-Fluorene Monomer

Compound I was synthesized as described below. Fluorene (0.54 mole), 2-naphthol (1.2 mole), 3-mercaptopropionic acid (0.0377 mole) and 300 mL of toluene were added into a reactor (1 L). 10 g of sulfuric acid was slowly and dropwise added into the reactor, and the compounds in the reactor were completely reacted at 80° C. for 10 hours. 100 g of toluene and 30 g of water were then added into the reactor, and the pH value of the mixture in the reactor was then tuned to 7 by 10% NaOH aqueous solution. The neutralized mixture was filtered, and the filtered cake was washed with water 5 times. The washed filtered cake was dried and re-crystallized from petroleum ether two times to obtain a white solid (yield=78%). The 1H NMR spectrum of the white solid is listed below: 1H NMR (CDCl3, 400 MHz, ppm): 7.94 (d, 2H), 7.62 (m, 8H), 7.37 (m, 6H), 7.10 (m, 4H).

The synthesis of naphthyl-fluorene monomer was similar to that of the phenyl-fluorene, thereby obtaining a white solid (yield=82%). The 1H NMR spectrum of the white solid is listed below: 1H NMR (CDCl3, 400 MHz, ppm): 8.82 (s, 2H), 8.69 (m, 4H), 7.96 (d, 2H), 7.65 (m, 8H), 7.40 (m, 6H), 7.15 (m, 4H). The above-mentioned reaction is represented as:

Example 3

Synthesis of Spiro-Fluorene Monomer

Compound II was synthesized as below. 9-fluorenone (60 mmole), resorcin (240 mmole), and zinc chloride (27.01 mmole) were weighted and mixed, and then heated to 140° C. and remained at 140° C. for 3 hours to be melted. 150 mL of concentrated hydrochloric acid was slowly added into the melted mixture to be refluxed for 2 hours. The reaction result was poured into 1 L of ice water to be precipitated. The precipitate was collected by filtration and then washed with n-hexane, and then re-crystallized from petroleum ether two times, thereby obtaining white solid (yield=70%). The 1H NMR spectrum of the white solid is listed below: 1H NMR (CDCl3, 400 MHz, ppm): 7.90 (d, 2H), 7.42 (dd, 2H), 7.23 (dd, 2H), 7.08 (d, 2H), 6.68 (d, 2H), 6.31 (d, 2H), 6.13 (d, 2H).

The synthesis of spiro-fluorene monomer was similar to that of the phenyl-fluorene, thereby obtaining a white solid (yield=82%). The 1H NMR spectrum of the white solid is listed below: 1H NMR (CDCl3, 400 MHz, ppm): 8.80 (s, 2H), 8.65 (m, 4H), 7.90 (d, 2H), 7.45 (dd, 2H), 7.26 (dd, 2H), 7.18 (d, 2H), 6.67 (d, 2H), 6.33 (d, 2H), 6.15 (d, 2H). The above-mentioned reaction is represented as:

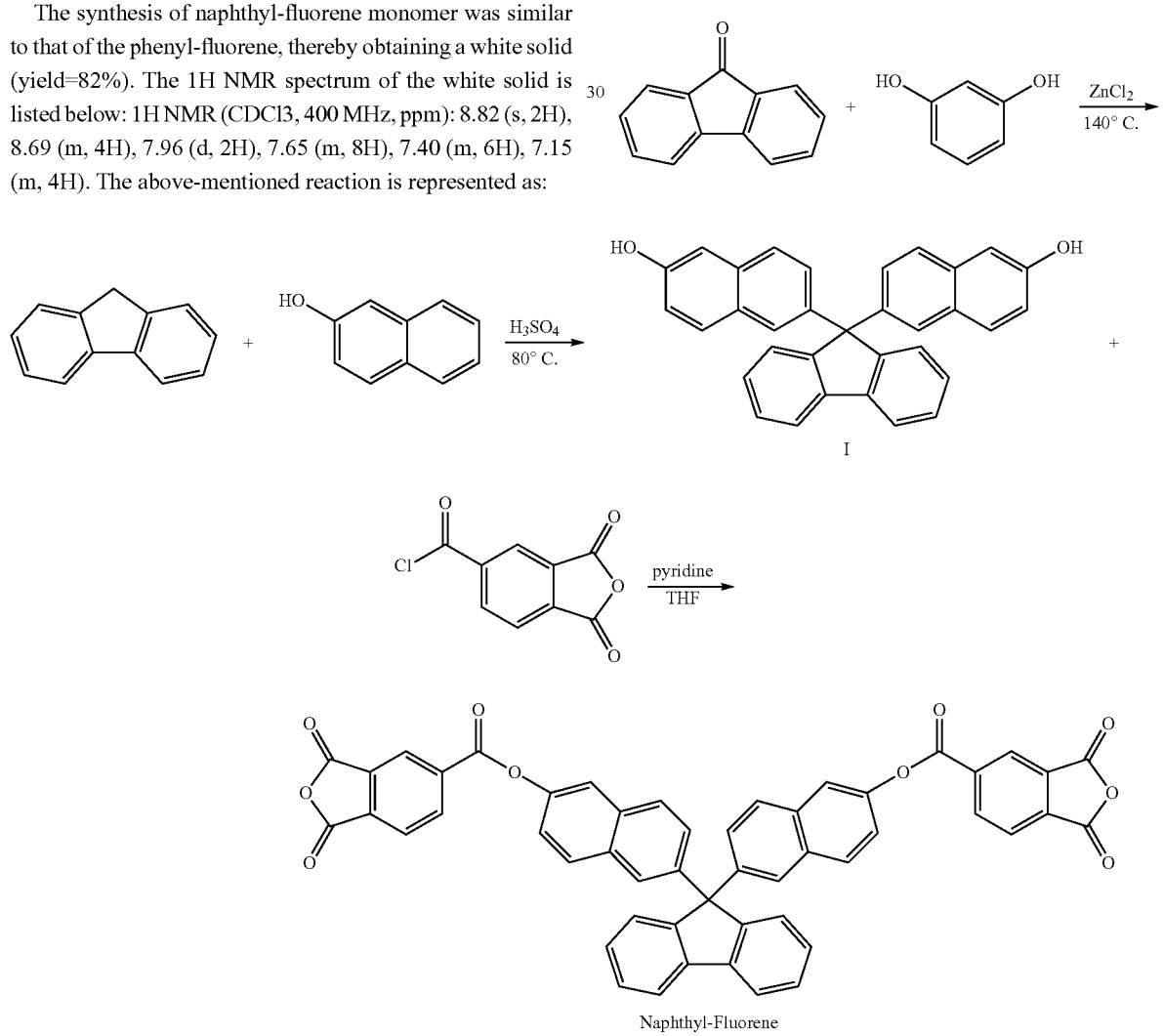

Naphthyl-Fluorene

-continued

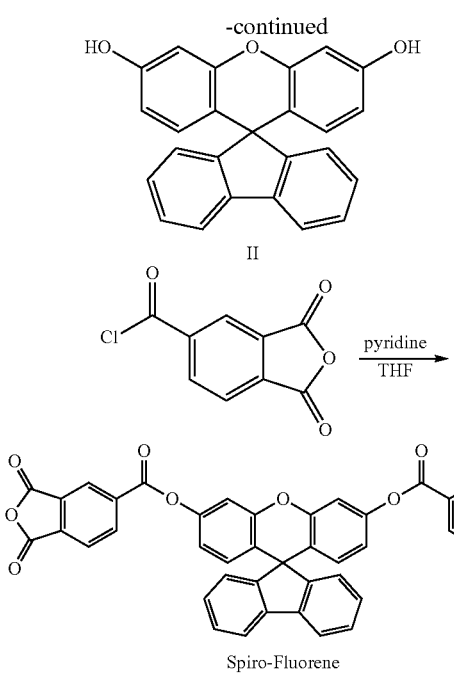

Spiro-Fluorene

Example 4

Synthesis of TPI Polymer

Phenyl-fluorene monomer (10 mmole) was added into a three-neck bottle and then dissolved by NMP. 4,4'-dihydroxy-diphenyl ether (10 mmole) was then added to the three-neck bottle, such that the solid content of the whole reaction is kept at 30%. The above reactants were reacted under nitrogen at room temperature for 24 hours, and appropriate toluene was then added thereto. Thereafter, the reaction was reacted at 200° C. for 12 hours. The toluene and water was removed out during the reaction by a Dean-Stark trap device. The reaction result was cooled to room temperature and then poured into methanol to be precipitated. The precipitate was collected by filtration and then dried. The dried precipitate was then dissolved in a small amount of NMP, and then precipitated in methanol. The precipitate was collected by filtration and dried as pale yellow solid (yield=95%). The 1H NMR spectrum of the pale yellow solid is listed below: 1H NMR (CDCl3, 400 MHz, ppm): 8.72 (s, 2H), 8.60 (d, 2H), 8.08 (d, 2H), 7.81 (d, 2H), 7.53-7.31 (m, 14H), 7.25-7.10 (m, 8H). The reaction is shown in Formula 8, wherein m represents the number of repetitions. The aforementioned product, polyimide, has a weight average molecular weight (Mw) of 73260, and molecular weight distribution is between 88172 and 59603. The thermal decomposition temperature (Td) of the polyimide is 471° C. so it is heat resistance material. The glass transition temperature (Tg) of the polyimide is 296° C. After biaxial stretching (the stretching ratio is 3, and the stretching temperature is 300° C.), the glass transition temperature (Tg) is 308° C. Therefore, the aforementioned PI has the advantages of heat resistance (high thermal decomposition temperature and a high glass transition temperature) and excellent hot workability.

(Formula 8)

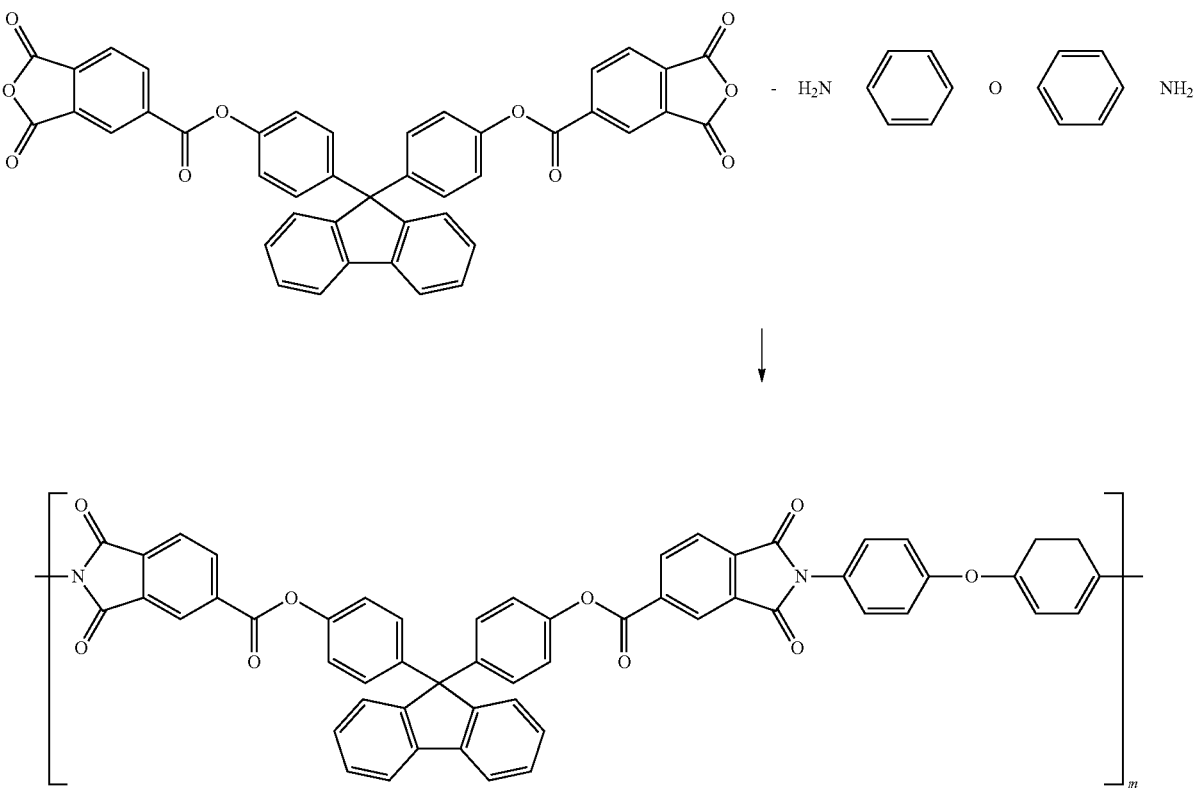

Example 5
Synthesis of TPI Polymer

Example 5 was performed in the similar manner as in Example 4 except that the phenyl-fluorene monomer of Example 1 was changed to the naphthyl-fluorene monomer of Example 2. The reaction of Example 5 is shown in Formula 9, wherein m represents the number of repetitions. The aforementioned product, polyimide, has a weight average molecular weight (Mw) of 64110, and molecular weight distribution is between 78311 and 51023. The thermal decomposition temperature (Td) of the polyimide is 485° C. so it is heat resistance material. The glass transition temperature (Tg) of the polyimide is 302° C. After biaxial stretching (the stretching ratio is 3, and the stretching temperature is 305° C.), the glass transition temperature (Tg) is 315° C. Therefore, the aforementioned PI has the advantages of heat resistance (high thermal decomposition temperature and a high glass transition temperature) and excellent hot workability.

(Formula 9)

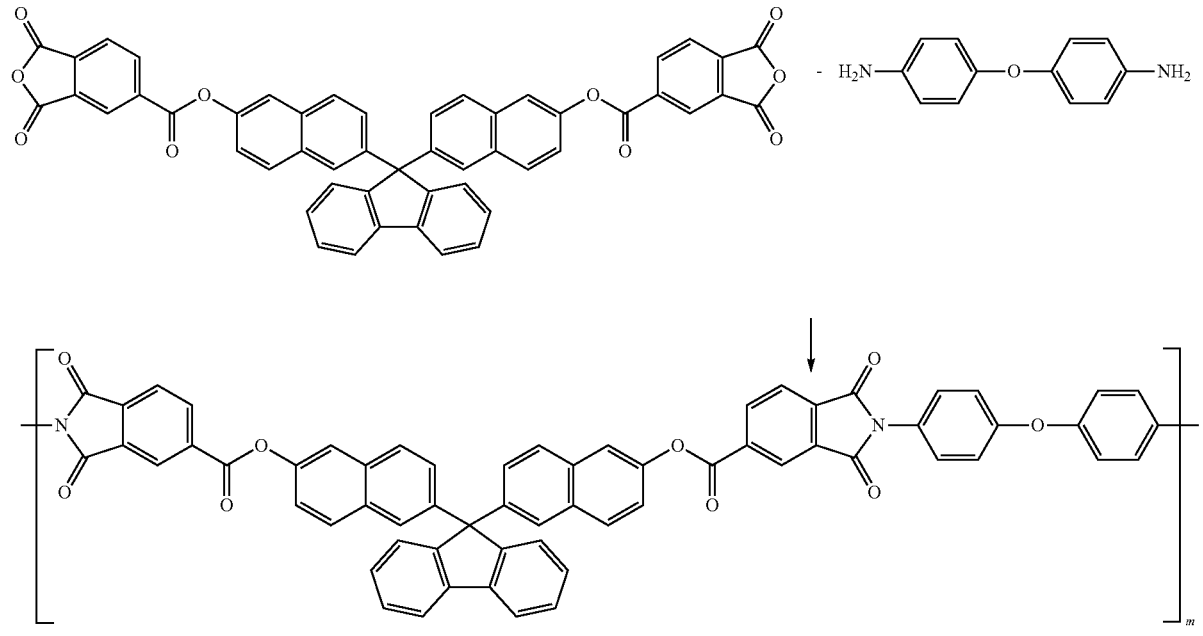

Example 6
Synthesis of TPI Polymer

Example 6 was performed in the similar manner as in Example 4 except that the phenyl-fluorene monomer of Example 1 was changed to Spiro-fluorene monomer of Example 3. The reaction of Example 6 is shown in Formula 10, wherein m represents the number of repetitions. The aforementioned product, polyimide, has a weight average molecular weight (Mw) of 43840, and molecular weight distribution is between 55631 and 32008. The thermal decomposition temperature (Td) of the polyimide is 481° C. so it is heat resistance material. The glass transition temperature (Tg) of the polyimide is 311° C. After biaxial stretching (the stretching ratio is 3, and the stretching temperature is 315° C., the glass transition temperature (Tg) is 319° C. Therefore, the aforementioned PI has the advantages of heat resistance (high thermal decomposition temperature and a high glass transition temperature) and excellent hot workability.

(Formula 10)

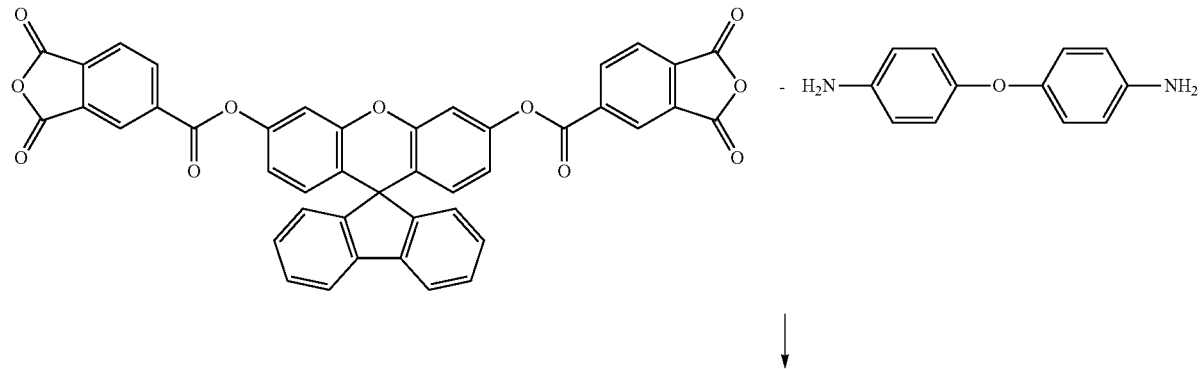

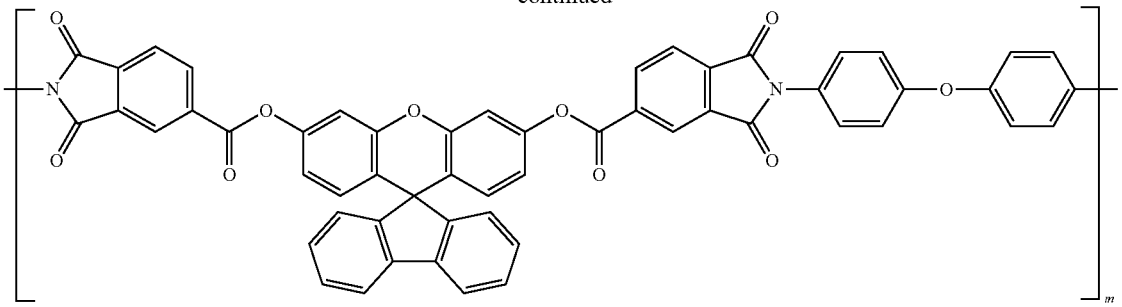

It will be apparent to those skilled in the art that various modifications and variations can be made to the disclosed embodiments. It is intended that the specification and examples be considered as exemplary only, with the true scope of the disclosure being indicated by the following claims and their equivalents.

What is claimed is:

1. A dianhydride, having a structure represented by Formula 1

(Formula 1)

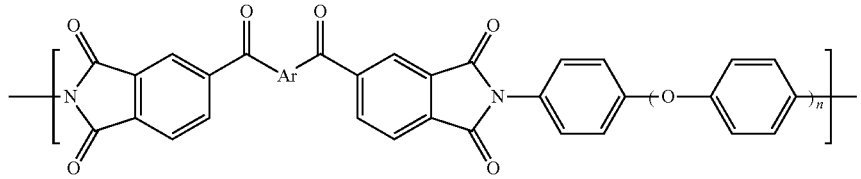

wherein Ar is

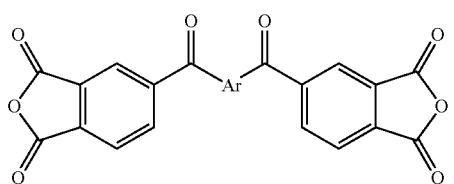

or

2. A polyimide comprising at least one repeating unit represented by formula 2:

(Formula 2)

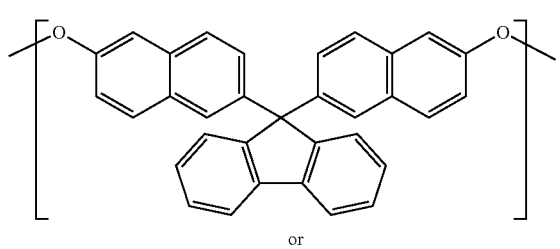

wherein Ar is

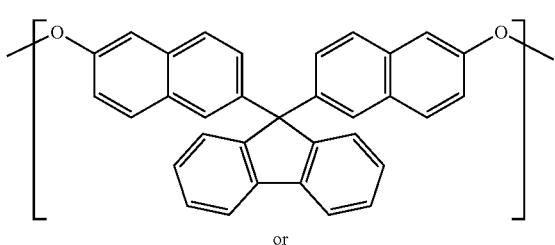

or

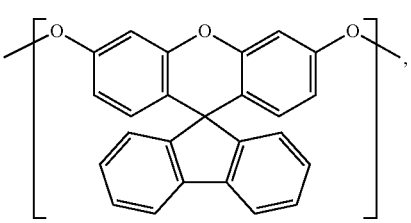

and n is an integer from 1 to 5.

3. The polyimide as claimed in claim 2, wherein n is an integer from 1 to 2.

4. The polyimide as claimed in claim 2, wherein the polyimide has a weight average molecular weight (Mw) of 20000 to 80000.

* * * * *